United States Patent
Arai et al.

(10) Patent No.: US 9,084,597 B2
(45) Date of Patent: Jul. 21, 2015

(54) SUTURE-BASED KNOTLESS REPAIR

(75) Inventors: Tatsuya Arai, Waltham, MA (US); Matthew Edwin Koski, Westford, MA (US)

(73) Assignee: SMITH & NEPHEW, INC., Memphis, TN (US)

(*) Notice: Subject to any disclaimer, the term of this patent is extended or adjusted under 35 U.S.C. 154(b) by 205 days.

(21) Appl. No.: 13/416,584

(22) Filed: Mar. 9, 2012

(65) Prior Publication Data

US 2013/0237997 A1    Sep. 12, 2013

(51) Int. Cl.
*A61B 17/04* (2006.01)

(52) U.S. Cl.
CPC ..... *A61B 17/0401* (2013.01); *A61B 2017/0409* (2013.01); *A61B 2017/0472* (2013.01); *A61B 2017/0474* (2013.01); *A61B 2017/0475* (2013.01)

(58) Field of Classification Search
CPC .......... A61B 17/0401; A61B 17/0469; A61B 17/0466; A61B 2017/0409; A61B 2017/0475; A61B 2017/0474; A61B 2017/0472; A61B 17/0642; A61B 2017/0406; A61B 2017/0404
USPC .......... 606/139, 144–148, 232, 222, 213, 228
See application file for complete search history.

(56) References Cited

U.S. PATENT DOCUMENTS

| | | |
|---|---|---|
| 3,580,256 A | 5/1971 | Wilkinson et al. |
| 4,605,414 A | 8/1986 | Czajka |
| 5,217,470 A | 6/1993 | Weston |
| 5,234,445 A | 8/1993 | Walker et al. |
| 5,306,301 A | 4/1994 | Graf et al. |
| 5,405,352 A | 4/1995 | Weston |
| 5,449,367 A | 9/1995 | Kadry |
| 5,451,203 A | 9/1995 | Lamb |
| 5,527,341 A | 6/1996 | Gogolewski et al. |
| 5,645,588 A | 7/1997 | Graf et al. |
| 5,690,649 A | 11/1997 | Li |
| 5,718,717 A | 2/1998 | Bonutti |
| 5,769,894 A | 6/1998 | Ferragamo |
| 5,893,592 A | 4/1999 | Schulze et al. |
| 5,989,252 A | 11/1999 | Fumex |
| 5,993,459 A | 11/1999 | Larsen et al. |
| 6,143,029 A | 11/2000 | Rippstein |
| 6,193,754 B1 | 2/2001 | Seedhom |
| 6,296,659 B1 | 10/2001 | Foerster |

(Continued)

FOREIGN PATENT DOCUMENTS

| | | |
|---|---|---|
| EP | 328401 | 8/1989 |
| EP | 2277456 | 1/2011 |

(Continued)

OTHER PUBLICATIONS

"Shoulder Restoration System: Y-Knot™ 1.3mm All-Suture Anchor," ConMed™ Linvatec, 2011, 4 pages.

(Continued)

*Primary Examiner* — Katrina Stransky
(74) *Attorney, Agent, or Firm* — Burns & Levinson LLP; Joseph M. Maraia

(57) ABSTRACT

An apparatus including a flexible member with two terminal ends configured to form a single closable loop and at least two fixation members. The first fixation member and the second fixation member are slidably received on the single closable loop formed by the flexible member.

22 Claims, 19 Drawing Sheets

(56) References Cited

U.S. PATENT DOCUMENTS

| | | | |
|---|---|---|---|
| 6,517,578 B2 | 2/2003 | Hein | |
| 7,390,329 B2 | 6/2008 | Westra et al. | |
| 7,390,332 B2* | 6/2008 | Selvitelli et al. | 606/232 |
| 7,601,165 B2 | 10/2009 | Stone | |
| 7,658,751 B2 | 2/2010 | Stone et al. | |
| 7,736,378 B2 | 6/2010 | Maahs et al. | |
| 7,749,250 B2 | 7/2010 | Stone et al. | |
| 7,771,455 B2 | 8/2010 | Ken | |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,959,650 B2 | 6/2011 | Kaiser et al. | |
| 7,972,292 B2 | 7/2011 | Behl et al. | |
| 8,057,511 B2 | 11/2011 | Flores et al. | |
| 8,088,130 B2 | 1/2012 | Kaiser et al. | |
| 8,118,836 B2 | 2/2012 | Denham et al. | |
| 8,128,640 B2 | 3/2012 | Harris et al. | |
| 8,128,658 B2 | 3/2012 | Kaiser et al. | |
| 8,137,382 B2 | 3/2012 | Denham et al. | |
| 8,172,871 B2 | 5/2012 | Ken | |
| 8,241,305 B2 | 8/2012 | Stone | |
| 8,298,262 B2 | 10/2012 | Stone et al. | |
| 8,303,604 B2 | 11/2012 | Stone et al. | |
| 8,308,765 B2 | 11/2012 | Saadat et al. | |
| 8,361,113 B2 | 1/2013 | Stone et al. | |
| 8,409,253 B2 | 4/2013 | Stone et al. | |
| 2001/0002440 A1 | 5/2001 | Bonutti | |
| 2001/0041938 A1 | 11/2001 | Hein | |
| 2002/0029066 A1 | 3/2002 | Foerster | |
| 2002/0115999 A1 | 8/2002 | McDevitt et al. | |
| 2003/0050666 A1 | 3/2003 | Grafton | |
| 2003/0130694 A1* | 7/2003 | Bojarski et al. | 606/228 |
| 2003/0149448 A1 | 8/2003 | Foerster et al. | |
| 2004/0133238 A1* | 7/2004 | Cerier | 606/232 |
| 2004/0181234 A1 | 9/2004 | McDevitt et al. | |
| 2004/0220573 A1 | 11/2004 | McDevitt et al. | |
| 2005/0033364 A1 | 2/2005 | Gregoire et al. | |
| 2005/0149118 A1 | 7/2005 | Koyfman et al. | |
| 2005/0187577 A1 | 8/2005 | Selvitelli et al. | |
| 2005/0209622 A1 | 9/2005 | Carrison | |
| 2005/0251159 A1 | 11/2005 | Ewers et al. | |
| 2005/0277985 A1 | 12/2005 | Wert et al. | |
| 2006/0155328 A1 | 7/2006 | Foerster | |
| 2006/0178680 A1 | 8/2006 | Nelson et al. | |
| 2006/0229671 A1 | 10/2006 | Steiner et al. | |
| 2006/0259076 A1 | 11/2006 | Burkhart et al. | |
| 2006/0293709 A1* | 12/2006 | Bojarski et al. | 606/232 |
| 2007/0010857 A1* | 1/2007 | Sugimoto et al. | 606/232 |
| 2007/0016244 A1 | 1/2007 | Behl et al. | |
| 2007/0083236 A1* | 4/2007 | Sikora et al. | 606/232 |
| 2007/0156174 A1 | 7/2007 | Kaiser et al. | |
| 2007/0185532 A1 | 8/2007 | Stone et al. | |
| 2007/0239209 A1 | 10/2007 | Fallman | |
| 2008/0065114 A1* | 3/2008 | Stone et al. | 606/139 |
| 2008/0140092 A1* | 6/2008 | Stone et al. | 606/144 |
| 2008/0140093 A1 | 6/2008 | Stone et al. | |
| 2008/0208204 A1 | 8/2008 | Schmieding et al. | |
| 2008/0208252 A1 | 8/2008 | Holmes | |
| 2008/0255557 A1 | 10/2008 | Koyfman et al. | |
| 2008/0255613 A1 | 10/2008 | Kaiser et al. | |
| 2008/0312689 A1 | 12/2008 | Denham et al. | |
| 2009/0036905 A1 | 2/2009 | Schmieding et al. | |
| 2009/0062846 A1 | 3/2009 | Ken | |
| 2009/0062847 A1 | 3/2009 | Ken | |
| 2009/0069823 A1 | 3/2009 | Foester et al. | |
| 2009/0082805 A1 | 3/2009 | Kaiser et al. | |
| 2009/0240335 A1 | 9/2009 | Arcenio et al. | |
| 2009/0248068 A1 | 10/2009 | Lombardo et al. | |
| 2009/0259260 A1* | 10/2009 | Bentley et al. | 606/300 |
| 2009/0306711 A1 | 12/2009 | Stone et al. | |
| 2009/0312776 A1 | 12/2009 | Kaiser | |
| 2009/0318961 A1 | 12/2009 | Stone et al. | |
| 2010/0023056 A1 | 1/2010 | Johansson et al. | |
| 2010/0114163 A1 | 5/2010 | Martin | |
| 2010/0130989 A1 | 5/2010 | Bourque et al. | |
| 2010/0145384 A1 | 6/2010 | Stone et al. | |
| 2010/0211075 A1 | 8/2010 | Stone | |
| 2010/0249809 A1 | 9/2010 | Singhatat et al. | |
| 2010/0256677 A1 | 10/2010 | Albertorio et al. | |
| 2010/0268273 A1 | 10/2010 | Albertorio et al. | |
| 2010/0268275 A1* | 10/2010 | Stone et al. | 606/232 |
| 2011/0009867 A1 | 1/2011 | Oren et al. | |
| 2011/0022061 A1* | 1/2011 | Orphanos et al. | 606/139 |
| 2011/0022083 A1 | 1/2011 | DiMatteo et al. | |
| 2011/0022084 A1 | 1/2011 | Sengun et al. | |
| 2011/0077667 A1 | 3/2011 | Singhatat et al. | |
| 2011/0098727 A1* | 4/2011 | Kaiser et al. | 606/144 |
| 2011/0098728 A1 | 4/2011 | McDevitt et al. | |
| 2011/0152885 A1 | 6/2011 | McDevitt et al. | |
| 2011/0152929 A1 | 6/2011 | McDevitt et al. | |
| 2011/0208239 A1* | 8/2011 | Stone et al. | 606/228 |
| 2011/0238111 A1 | 9/2011 | Frank | |
| 2011/0264141 A1 | 10/2011 | Denham et al. | |
| 2011/0270278 A1 | 11/2011 | Overes et al. | |
| 2012/0046693 A1 | 2/2012 | Denham et al. | |
| 2012/0053630 A1 | 3/2012 | Denham et al. | |
| 2012/0059417 A1 | 3/2012 | Norton | |
| 2012/0116450 A1 | 5/2012 | McDevitt et al. | |
| 2012/0130422 A1 | 5/2012 | Hootstein | |
| 2012/0150297 A1 | 6/2012 | Denham et al. | |
| 2012/0197271 A1* | 8/2012 | Astorino et al. | 606/148 |
| 2012/0215257 A1 | 8/2012 | McDevitt et al. | |
| 2012/0239085 A1 | 9/2012 | Schlotterback et al. | |
| 2012/0290004 A1* | 11/2012 | Lombardo et al. | 606/232 |
| 2013/0018416 A1 | 1/2013 | Lombardo et al. | |
| 2013/0023930 A1 | 1/2013 | Stone et al. | |
| 2013/0035722 A1 | 2/2013 | McDevitt et al. | |
| 2013/0110165 A1* | 5/2013 | Burkhart et al. | 606/232 |
| 2013/0123810 A1 | 5/2013 | Brown et al. | |
| 2013/0123813 A1 | 5/2013 | Stone et al. | |
| 2013/0138123 A1 | 5/2013 | Stone et al. | |
| 2013/0158601 A1 | 6/2013 | Stone et al. | |
| 2013/0237997 A1 | 9/2013 | Arai et al. | |
| 2014/0114330 A1 | 4/2014 | Karasic et al. | |

FOREIGN PATENT DOCUMENTS

| | | |
|---|---|---|
| FR | 2743294 | 7/1997 |
| GB | 2370227 | 11/2003 |
| WO | 03092551 | 11/2003 |
| WO | 2004037094 | 5/2004 |
| WO | 2006086275 A2 | 8/2006 |
| WO | 2007005394 A1 | 1/2007 |
| WO | 2012048050 A1 | 4/2012 |
| WO | 2012103536 A1 | 8/2012 |
| WO | 2012112793 A1 | 8/2012 |
| WO | 2014062684 A1 | 4/2014 |

OTHER PUBLICATIONS

"Should Restoration System: Arthroscopic Bankart Repair Using the Y-Knot™ 1.3mm All-Suture Anchor," ConMed™ Linvatec, 2011, 4 pages.

"Technique for ACL reconstruction with Acufex Director Drill Guide and Endobutton CL" copyright 1999, Smith & Nephew, Inc., 20 pages.

"Endobutton Direct: Fixation Device," Smith & Nephew, Inc., reprinted from http://global.smith-nephew.com/us/product23376_5895.htm, on Nov. 22, 2010, 3 pages.

"Endobutton CL," Smith and Nephew, Inc., reprinted from http://endo.smith-nephew.com/es/Standard.asp?NodeID=2715, on Nov. 22, 2010, 1 page.

From, Stuart, "ACL Reconstruction with Bone-Tendon-Bone Transplants using the Endobutton CL BTB Fixation System," Smith & Nephew, Inc., copyright 2004, printed on Apr. 4, 11 pages.

Scope This Out, vol. 10, No. 2, Summer 2008, 8 pages.

Scope This Out, vol. 12, No. 2, Fall 2010, 8 pages.

Scope this Out, vol. 12, No. 1, Spring 2010, 8 pages.

ToggleLOC: Femoral Fixation Device with Zip Loop Technology, Biomet Sports Medicine, Inc., 2007, 8 pages.

Glousman, R., et al., "JuggerKnot Soft Anchor Surgical Technique," Biomet Sports Medicine, 2010, 1 page.

(56) References Cited

OTHER PUBLICATIONS

Game Plan: Innovative Products to be Launched AAOS 2010, Biomet Sports Medicine, Spring 2010, vol. 2, No. 3, 1 page.

Lawhorn, K., "MaxFire MarXmen Device Surgical Technique," Biomet Sports Medicine, 2010, 1 page.

International Search Report and Written Opinion for International Application No. PCT/US2012.023056, mailed Jun. 13, 2012.

International Search Report Application No. PCT/US2013/029143, mailed Jun. 13, 2013.

International Search Report Application No. PCT/US2013/065064, mailed Feb. 21, 2014.

* cited by examiner

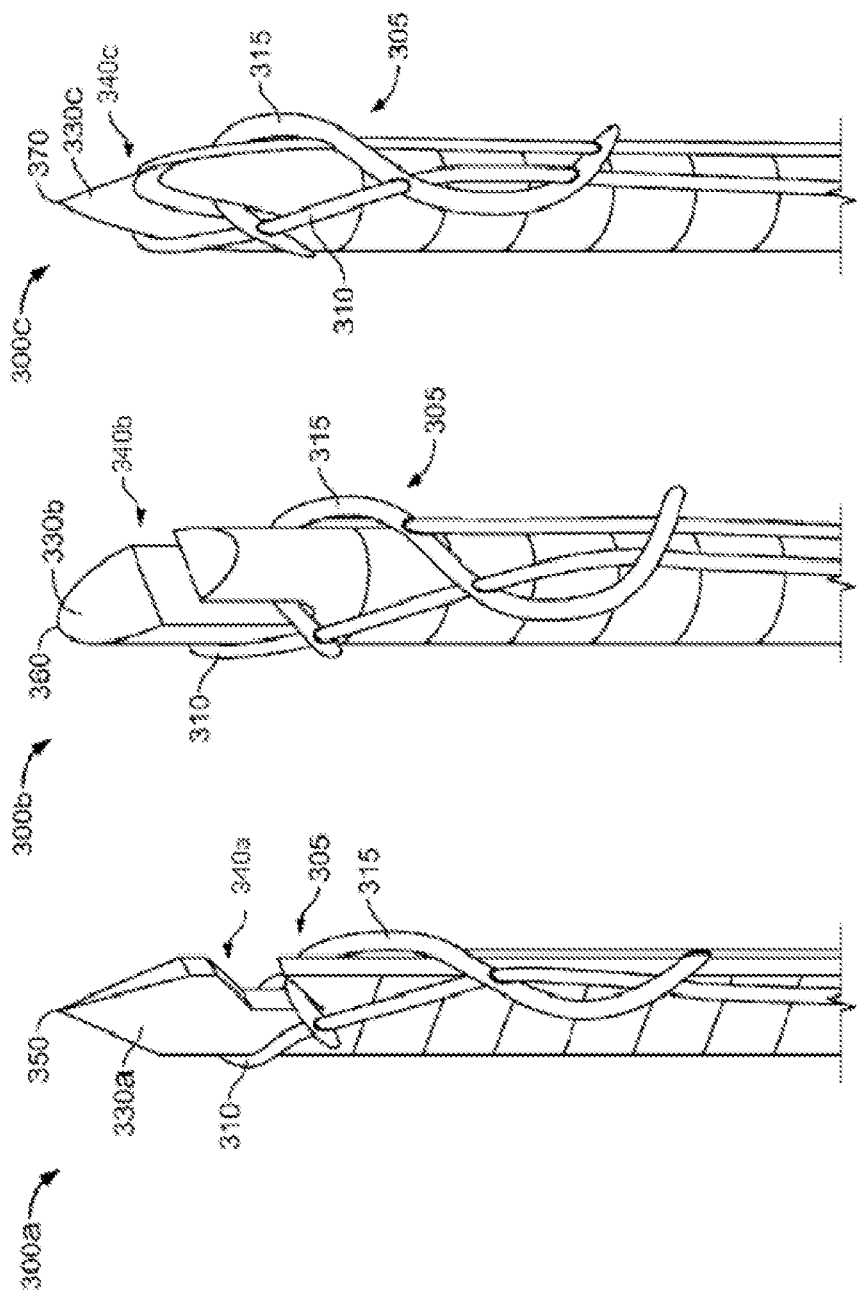

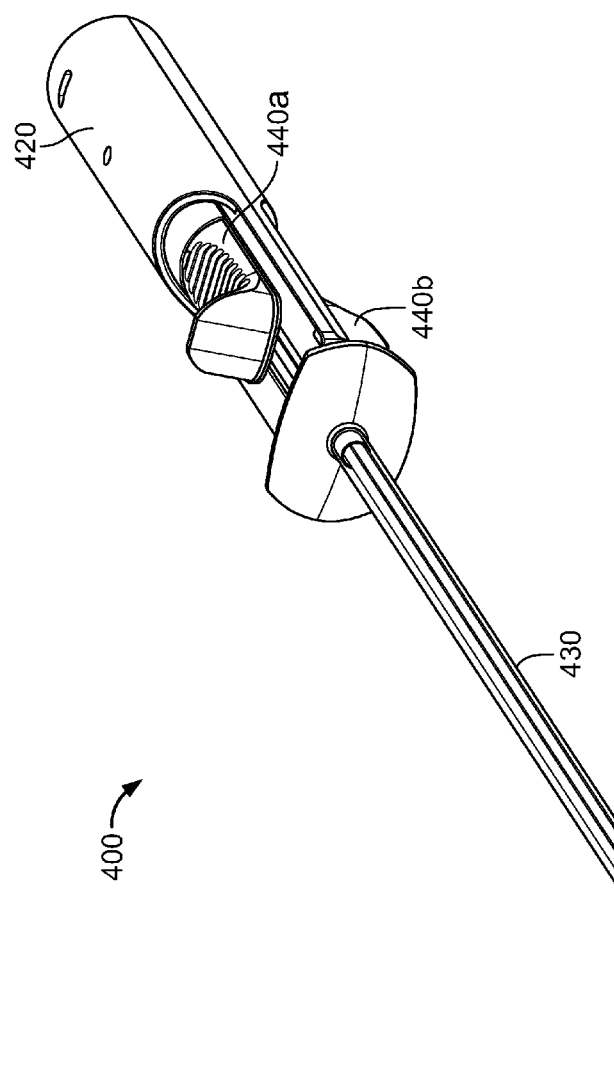
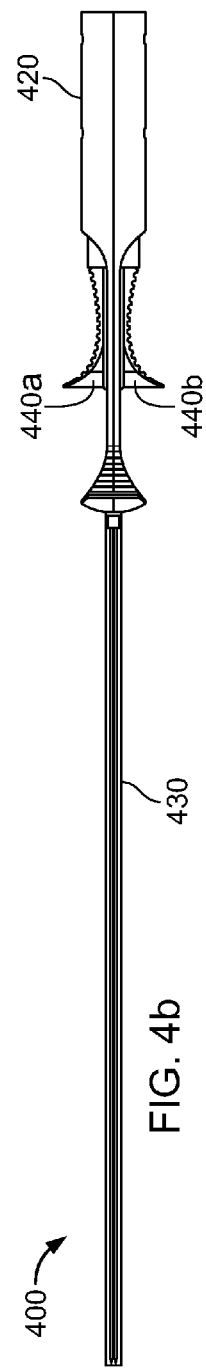

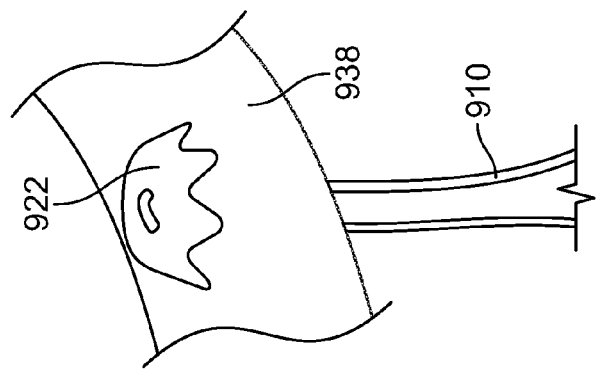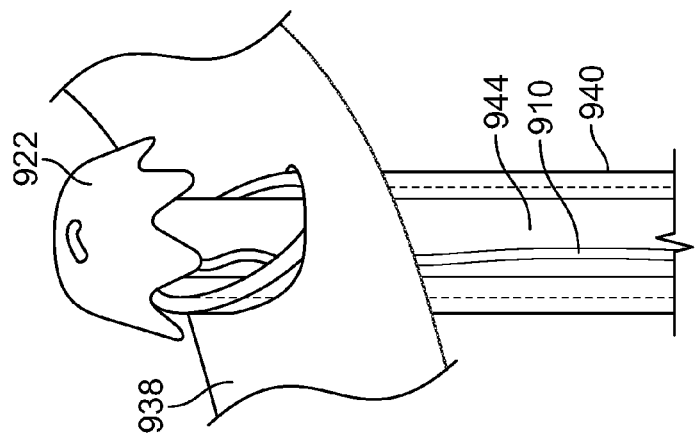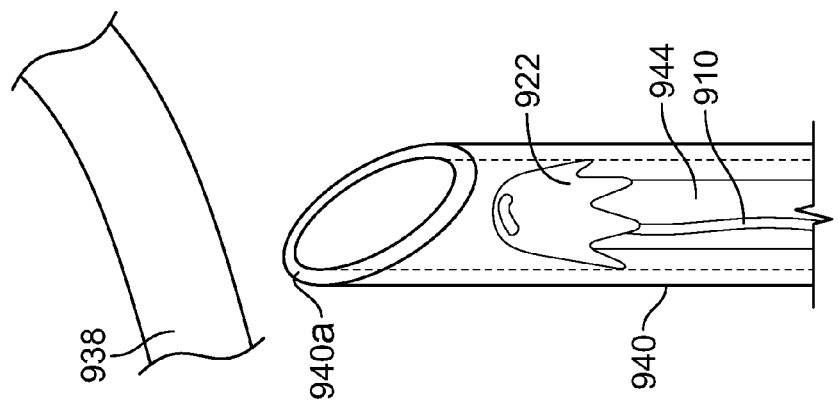

SUTURE-BASED KNOTLESS REPAIR

TECHNICAL FIELD

This application relates to devices and methods for repairing tissue.

BACKGROUND

Fibrous tissue wounds, such as muscle, ligament, and cartilage tears, can be repaired arthroscopically. To close a fibrous tissue wound, a surgeon can insert two suture needles into the tissue with sutures attached, thread the sutures across the wound, sometimes using an anchor, and then tie knots to fix the free ends of the sutures within the tissue.

In these repairs, there is a clinical need to reduce steps and complexity to shorten duration of surgery. In particular, knot tying entails complex and time-consuming steps such as shuttling sutures, wires, and suture passers through cannulas.

To simplify the wound closure procedure a knotless suture-based repair system has been developed.

SUMMARY

A suture-based repair system of the present disclosure eliminates tying a knot during a surgery, such as labral repair, or other tissue repair. The system utilizes a simple linear motion to close the wound and is intuitive and can reduce overall surgical time. The system can be used to repair tissue and improve, for example, shoulder and hip stability, and can be used for any repair that takes advantage of one or more suture anchoring techniques, including hip, knee, and rotator cuff repair.

In one general aspect, an apparatus includes a flexible member with two terminal ends, a first fixation member, and a second fixation member. The flexible member forms a single closable loop and the first fixation member and the second fixation member are slidably received on the single closable loop formed by the flexible member.

Implementations may include one or more of the following features. For example, the length of the single closable loop may be shortened when tension is applied to one of the terminal ends of the flexible member. The flexible member may comprise a suture. The first fixation member and the second fixation member may be flexible. The first fixation member and the second fixation member may be sutures. The first fixation member and the second fixation member may be rigid. The first fixation member may be flexible and the second fixation member may be rigid. A third fixation member may be coupled to one terminal end of the flexible member.

In another general aspect, a surgical assembly includes a delivery device and a surgical device. The delivery device includes a handle, an outer tube, a first insertion needle, and a second insertion needle. The outer tube is coupled to the handle and extends from the handle. The first and second insertion needles are at least partially slidably disposed within the outer tube. The surgical device includes a flexible member, a first fixation member, and a second fixation member. The flexible member has two terminal ends and forms a single closable loop. The first fixation member and the second fixation member are slidably received on the single closable loop formed by the flexible member such that pulling on a terminal end of the flexible member shortens a length of the flexible member between the first fixation member and second fixation members. The first fixation member is releasably secured to the first insertion needle and the second fixation member is releasably secured to the second insertion needle.

Implementations may include one or more of the following features. For example, the first fixation member and the second fixation member may be flexible fixation members or sutures. The first insertion needle may define a notch that receives the first fixation member and the second insertion needle may define a notch that receives the second fixation member, so that the first fixation member is releasably secured to the first insertion needle by inserting a portion of the first fixation member into the notch defined by the first insertion needle and the second fixation member is releasably secured to the second insertion needle by inserting a portion of the second fixation member into the notch defined by the second insertion needle. The surgical assembly may also include a first and a second switch slidably positioned within the handle and coupled to the first insertion needle and second insertion needle, respectively.

In another general aspect, a surgical assembly includes a delivery device and a surgical device. The delivery device includes a handle, a tubular needle, and a pusher. The tubular needle extends from the handle and defines a longitudinal channel and a trocar tip. The pusher is disposed at least partially within the tubular needle. The surgical device includes a flexible member with two terminal ends, a first fixation member, and a second fixation member. The flexible member forms a single closable loop. The first fixation member and the second fixation member are slidably received on the single closable loop such that pulling on a terminal end of the flexible member shortens a length of the flexible member between the first fixation member and the second fixation member. The first fixation member is secured to the pusher. The second fixation member is positioned adjacent to an outer surface of the tubular needle and the flexible member passes through the longitudinal channel.

Implementations may include one or more of the following features. For example, the pusher may define a notch configured to receive the first fixation member so that the first fixation member is secured to the pusher by inserting a portion of the first fixation member into the notch defined by the pusher. The surgical assembly may include a switch slidably positioned within the handle. The switch may be coupled to a proximal end of the pusher. The first fixation member may be a flexible fixation member and the second fixation member may be a rigid fixation member. The first fixation member is a suture. The pusher may be an inserter needle.

In another general aspect, a method of repairing labral tissue includes implanting a first fixation member into tissue at a first location, passing a flexible member across a wound, and implanting a second fixation member into tissue at a second location. The first fixation member and the second fixation member are slidably received on a single closable loop formed by the flexible member such that pulling on a terminal end of the flexible member shortens a length of the single closable loop.

Implementations may include one or more of the following features. For example, the tissue at the first location is soft tissue and the tissue at the second location may be bone tissue. The tissue at the first location may be soft tissue and the tissue at the second location may be soft tissue. The tissue at the first location may be bone tissue and the tissue at the second location may be bone tissue.

Other features will be apparent from the description and drawings, and from the claims.

BRIEF DESCRIPTION OF THE DRAWINGS

FIGS. 3a-3d are schematics of different implementations of insertion needles.

FIG. 4a is a perspective view of a deployment device for use with a suture-based knotless repair system.

FIG. 4b is a side view of the deployment device of FIG. 4a.

FIG. 4c is a partial cutaway view of the insertion needles in the deployment device of FIG. 4a.

FIG. 4d is an end view of the deployment device of FIG. 4a.

FIG. 4e is an end perspective view of the deployment device of FIG. 4a.

FIGS. 9a-9g illustrate another implementation of a suture-based knotless repair system.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood, of course, that this disclosure is not limited to the particular implementations illustrated herein.

DETAILED DESCRIPTION

Figure 1:
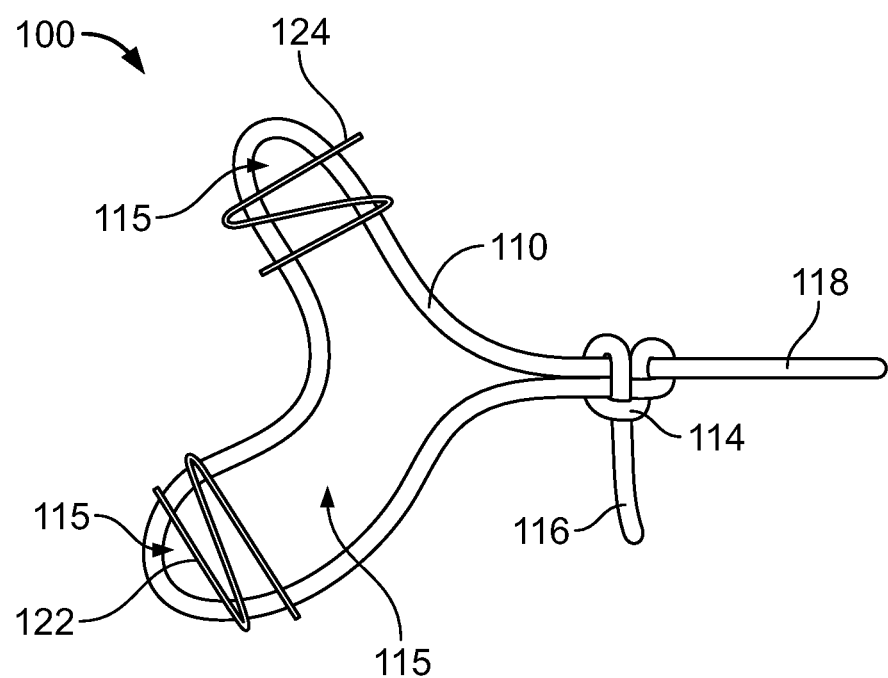
FIGS. 1 and 2a are schematics of a suture-based knotless repair system in an open configuration.
Figure 2A:
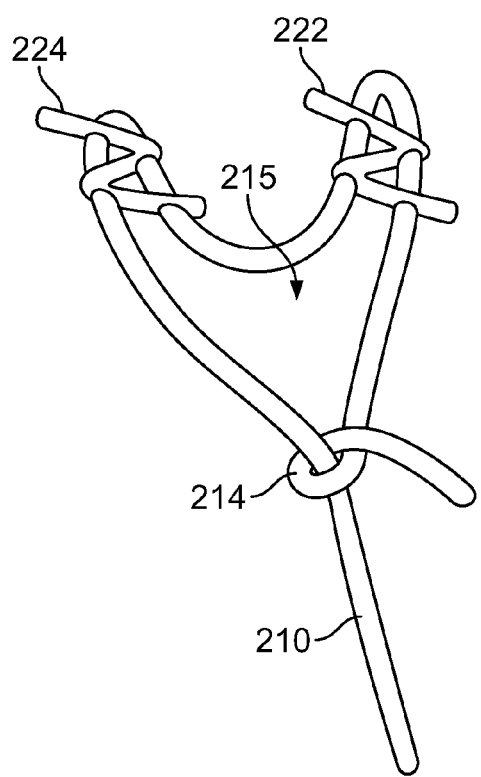
Figure 2B:
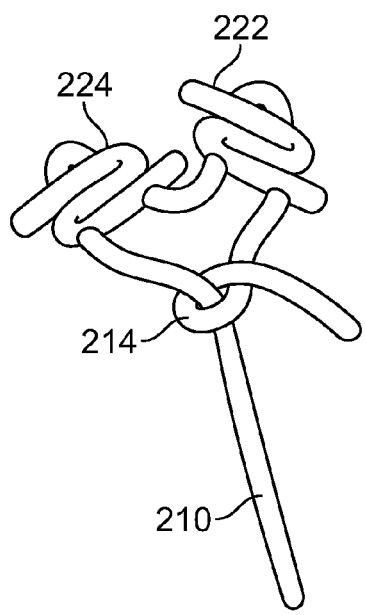
FIG. 2b is a schematic of a suture-based knotless repair system in a closed configuration.

FIGS. 1, 2a, and 2b show a suture-based repair system 100 that assists in eliminating knot tying during surgical procedures, such as labral repair, or other tissue repair. A flexible member 110, such as a suture, forms a single loop 115 with a fixed terminal end 116 and a sliding terminal end 118. At least two fixation members, or anchors, 122 and 124 are connected to the suture 110 along portions of the suture 110 forming the single loop 115. The anchors 122, 124 are slidable with respect to the suture 110, and likewise, the suture 110 is slidable with respect to the anchors 122, 124. The loop 115 of the suture 110 can be closed by, for example, use of a slipknot 114, such as a KINSA™/FASTFIX™ knot as described in, for example, U.S. Pat. No. 7,651,509, entitled "Methods and Devices for Tissue Repair," which is incorporated herein by reference in its entirety, or any applicable sliding or slip knot.

As will be described in more detail below, in use, when the sliding terminal end 118 of the suture 110 is pulled, the loop 115 decreases in size, bringing the anchors 122 and 124 closer together. Referring to FIGS. 2a and 2b, the placement of two anchors 222 and 224 on a single loop 215 of the suture 210 allows the anchors 222 and 224 to be brought very close together when the loop is closed (FIG. 2b). With such a configuration, it is possible to virtually eliminate the distance between the anchors 222 and 224 along a length of the suture 210. In addition, such a construct provides infinite adjustability and/or tightening of suture slack between the anchors, which provides for a higher degree of fixation. This configuration also can provide a significant advantage in labral repairs, because an anchored labrum can be shifted as close to an anchored glenoid as possible.

Figure 3D:
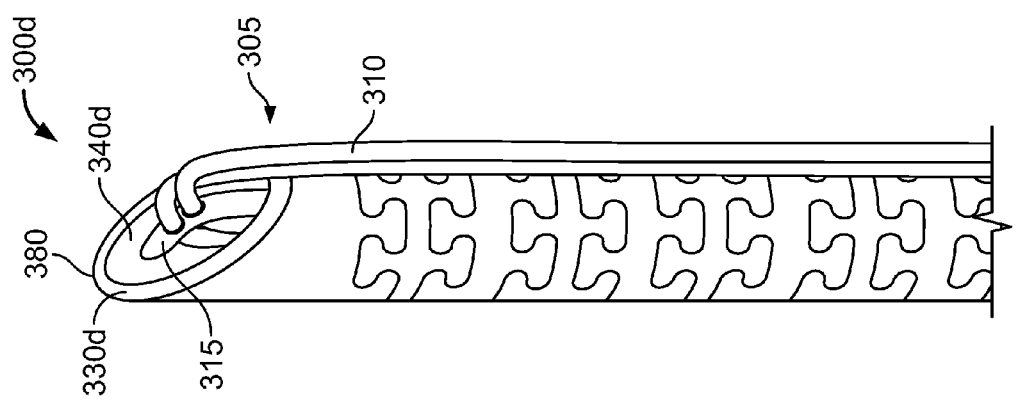

Referring to FIGS. 3a-3d, a delivery device 300a, 300b, 300c, and 300d, respectively, for deploying and implanting a suture-based knotless repair system 305, which includes a suture 310 and one or more anchors 315, in tissue includes an inserter needle 330a, 330b, 330c, and 330d, respectively. The inserter needles 330a, 330b, 330c, and 330d include notches 340a, 340b, and 340c, respectively, or a hole 340d, defined in a distal tip 350, 360, 370, and 380 of the needles 330a, 330b, 330c, and 330d. In use, the notches 340a, 340b, 340c, and or hole 340d receive at least one of the anchors 315 such that the anchors 315 can be retained within the notches 340a, 340b, 340c or the hole 340d, during, for example, delivery of the repair system 305 to the surgical site. The notches 340a, 340b, and 340c and the hole 340d open towards the distal end of the needles 330a, 330b, 330c, and 330d and this so-called "forward-facing" design allows the anchor 315 to remain in the notch 340a, 340b, and 340c and the hole 340d during insertion into tissue, and allows the inserter needle 330a, 330b, 330c, and 330d to be retracted from the tissue, such as the glenoid and labrum/capsule, once the anchor 315 has been deployed, without disturbing the deployed anchor 315 in the tissue. The suture 310 may be wrapped around the back of the inserter needle 330a, 330b, and 330c as shown in FIGS. 3a-3c, respectively, to further aid in holding the anchor 315 in place within the notches 340a, 340b, and 340c during delivery. Holding the anchor 315 in the notch also can help to limit deformation of the flexible anchor 315, like that shown in FIGS. 3a-3c, before the anchor 315 has been placed into tissue by the surgeon.

The inserter needles 330a, 330b, and 330c may be of various shapes including rectangular cross-sectional, such as needle 330a, or circular cross-sectional, such as needles 330b and 330c. The needles 330a, 330b, 330c, and 330d can also be formed with a variety of tip shapes, such as a converging sharpened tip (350, 370) and a rounded, flattened tip (360, 380). The needles 330a, 330b, 330c, and 330d are generally made from metal, but can be made from any other suitable biocompatible materials, such as hardened plastic. The inserter needles 330a, 330b, and 330c can take any number of shapes, such as linear, curved, twisted, segmented, partially sliced, puzzle-cut, and can include a trocar-tipped tube configuration.

Referring to FIGS. 4a-4e, two or more inserter needles 410, 415 (similar to, for example, inserter needles 330a in FIG. 3a) are located within a delivery device 400. The delivery device 400 includes a handle 420 coupled to an outer tube or cannula 430. The outer tube 430 can be made from plastic or metal. The handle 420 includes two actuating sliders 440a, 440b slidably disposed on opposite sides of the handle 420. The sliders 440a, 440b are coupled to a proximal end (not shown) of the inserter needles 410, 415 for advancing and retracting the inserter needles 410, 415 within the outer tube 430. The distance that the inserter needles 410, 415 extend from the outer tube 430 helps to determine the penetration depth of the needles 410, 415 into tissue. In some implementations, the delivery device 400 can be supplied to the surgeon with the suture-based anchor system preloaded in the device 400.

Figure 4C:
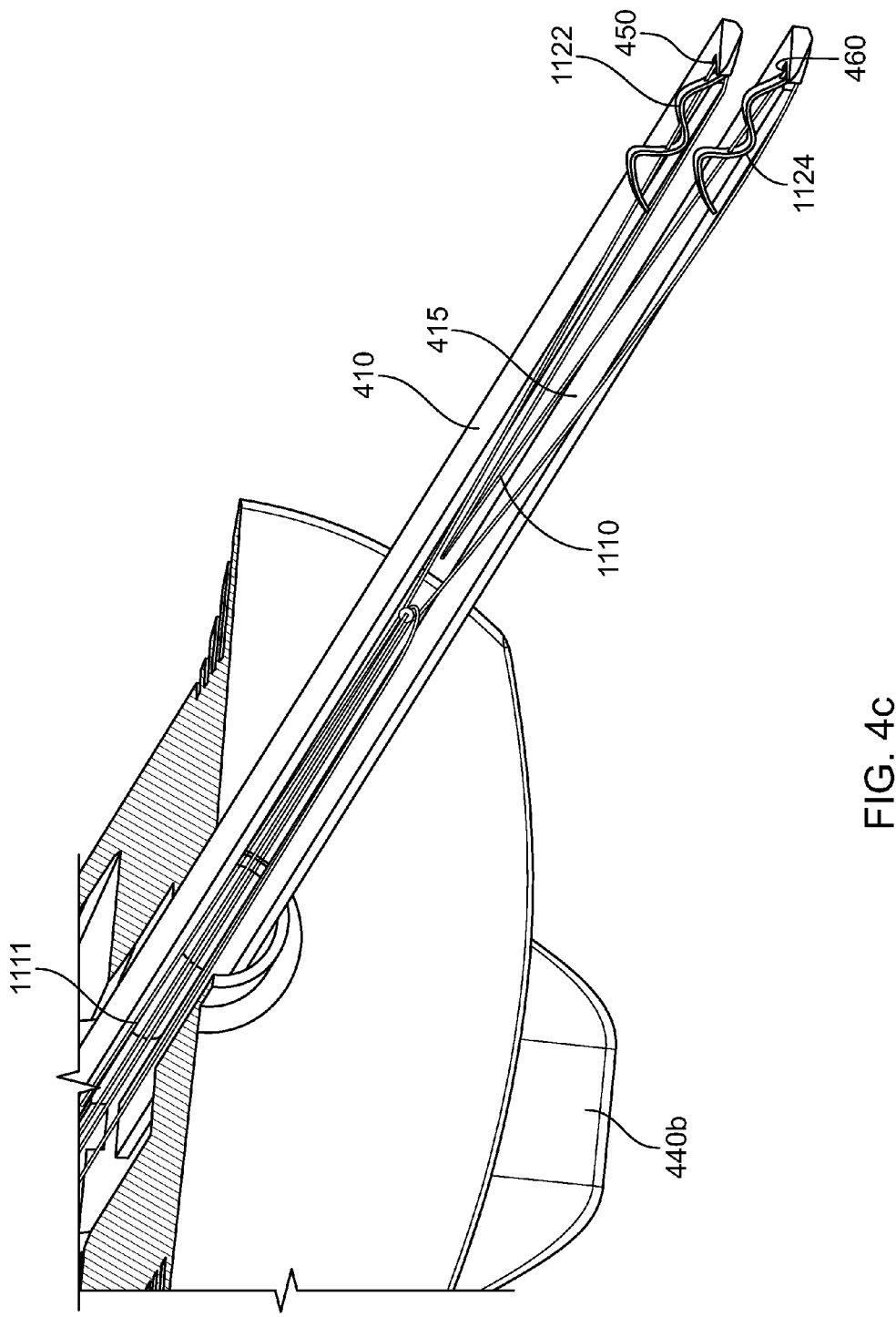
Figure 4D:
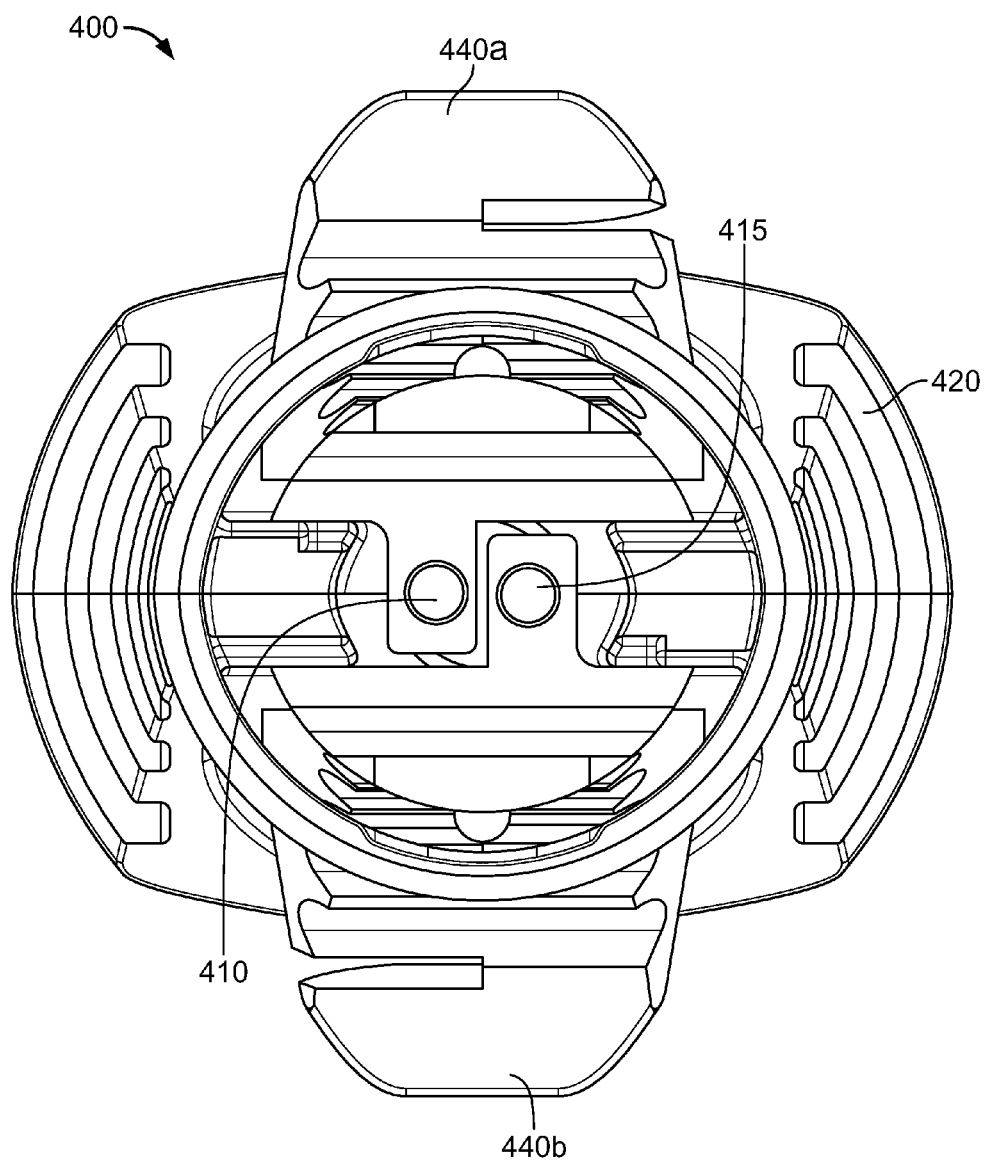

Referring to FIG. 4c, the inserter needles 410 and 415 are shown with anchors, such as suture anchors 1122, 1124, loaded in the notches 450 and 460, respectively. The anchors 1122 and 1124 are attached to a single loop 1115 of suture 1110. In this implementation, a second suture 1111 is used to engage and tension a portion of the first suture 1110, for example, the single loop 1115, during delivery and surgery to assist in preventing one of the anchors 1122 and 1124 from slipping out of the notches 450 and 460, while, for example, another of the anchors is being advanced through the outer tube 430 and into tissue. The user may remove the second suture 1111 from the system after inserting the anchors 1122 and 1124 into tissue.

Figure 4E:
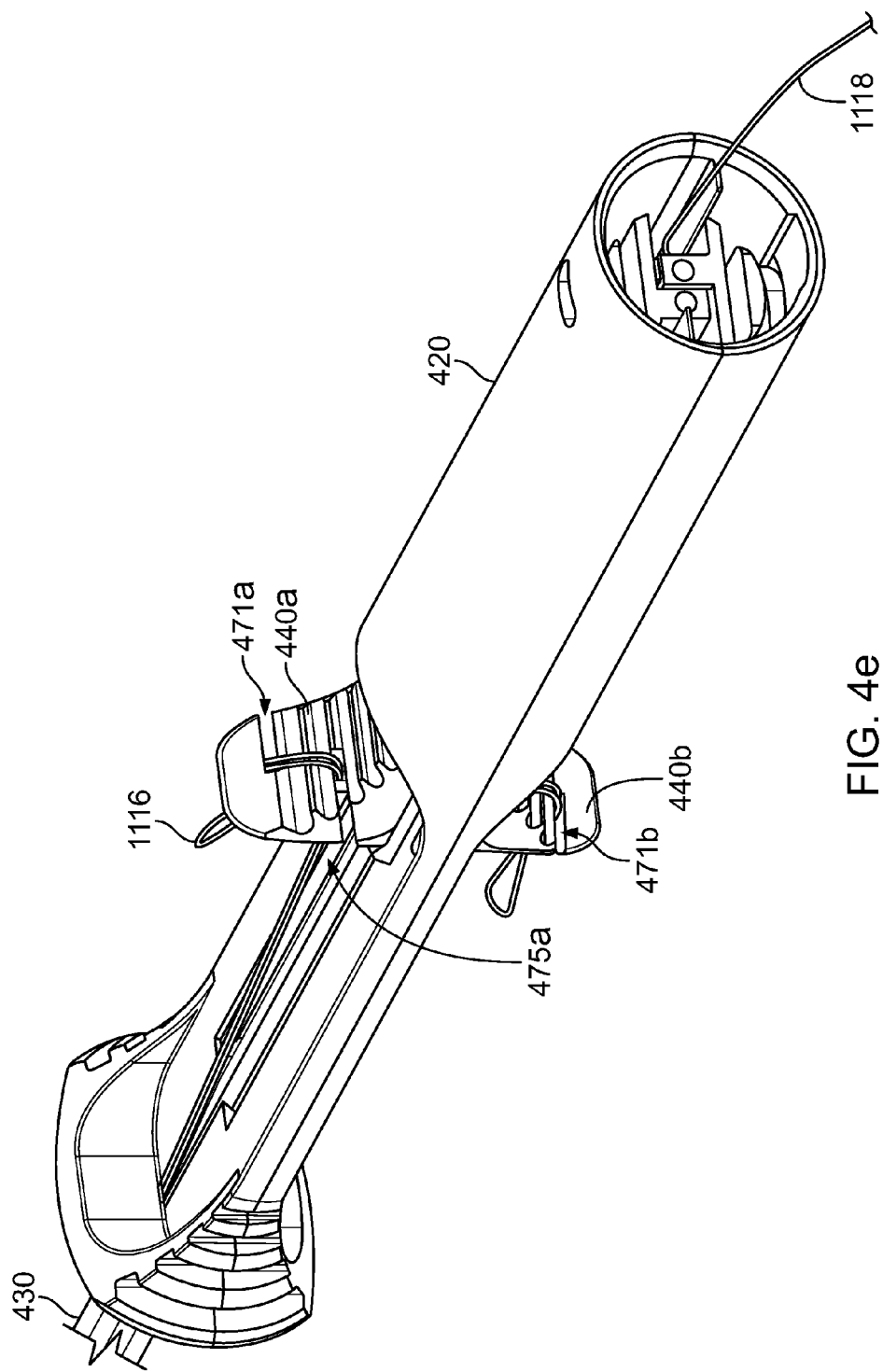

Referring to FIG. 4e, sliding end 1118 of the suture 1110 can exit the outer tube 430 and pass through a longitudinal slot 475a in the handle 420. The sliders 440a, 440b can include one or more slots 471a and 471b that can be used to secure a fixed terminal end 1116 of the suture 1110 such that when a surgeon advances sliders 440a or 440b, the fixed end 1116 does not move relative to the slider, which permits the sutures 1112 or 1124 to come off the notches 450 or 460 (FIG. 4C).

Figure 5A:
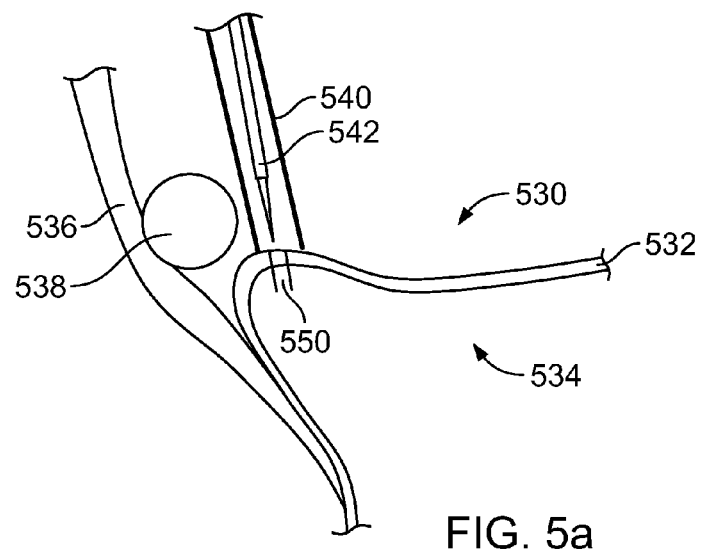
FIGS. 5a-5g are schematics showing a uni-cortical method of using a suture-based knotless repair system.
Figures 5B, 5C:
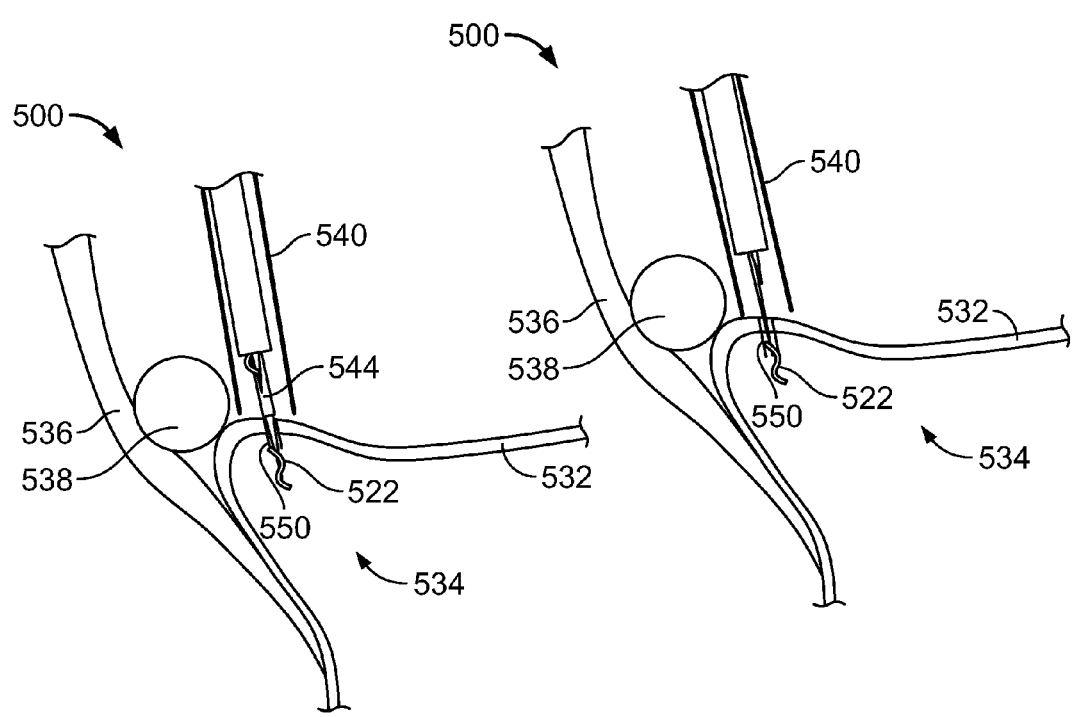
Figure 5D:
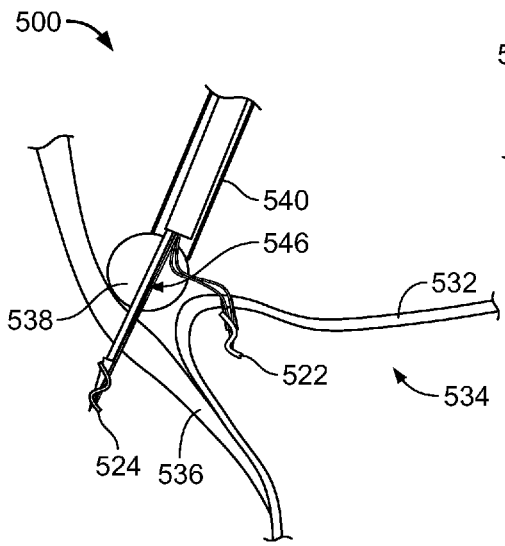

Referring to FIGS. 5a-5g, a method for using a suture-based knotless repair system 500 to make a uni-cortical labral repair, for example, in the shoulder area 530, is shown. The repair system 500 includes a suture 510 and at least two anchors 522, 524 coupled to the suture 510, and in particular, to a single loop 515 (FIG. 5f) formed by the suture 510. The suture 510 has a fixed terminal end 516 and a sliding terminal end 518 as described above (FIG. 5f). In use, preferably under arthroscopic guidance, a user inserts a drill 542 (FIG. 5a) through a guide 540 to drill a hole 550 through glenoid cortex bone 532 and into cancellous bone tissue 534. The guide can be straight or curved. The user can then use a first inserter needle 544 to pass the anchor 522 through the glenoid cortex bone 532 and into the cancellous bone tissue 534 (FIG. 5b). When the first inserter needle 544 is removed from the tissue 534 (FIG. 5c), the anchor 522 is left behind. The guide 540 is then moved and the drill can again be used (not shown) to drill a hole 552 in the labrum 538 and the capsule 536.

Figure 5E:
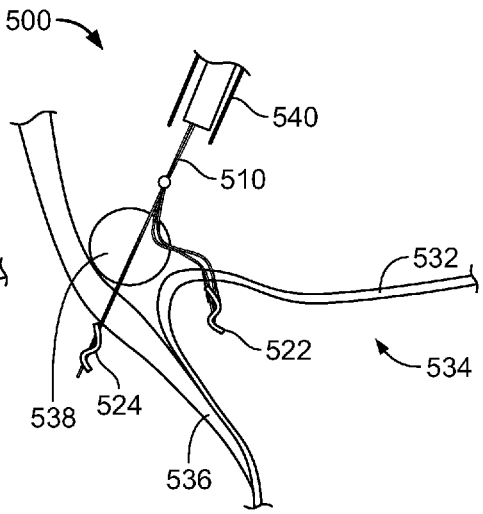
Figure 5F:
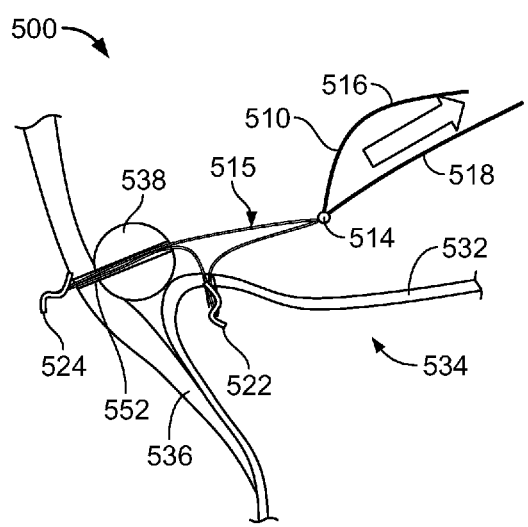
Figure 5G:
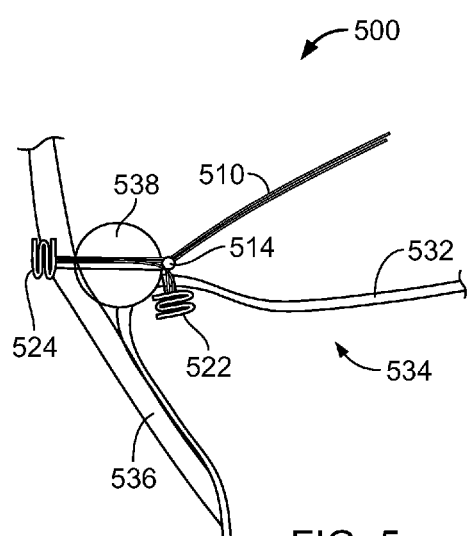

A second inserter needle 546 can be used to pass a second anchor 524 through the labrum 538 and capsule 536. When the second inserter needle 546 is removed, the second anchor 524 is left behind (FIG. 5e). Once each of the anchors 522 and 524 have been deployed into the tissue, the user may pull the sliding terminal end 518 of the suture 510 to shorten the length of the loop 515 thus bringing the anchors 522 and 524 closer together. If flexible anchors, such as the suture anchors 522, 524 shown, are used, the anchors will tend to bunch up as seen in FIG. 5g when force is applied to the anchors 522 and 524 from the loop 515 being pulled closed. The bunching up of the anchors 522, 524 assist in preventing pull-out of the anchors when the sliding terminal end 518 of the suture 510 is pulled, and provides for a more secure repair construct. A knot pusher (not shown) may also be used in conjunction with pulling on the sliding end 518 of the suture 510 to aid in closing the loop 515.

Figure 6A:
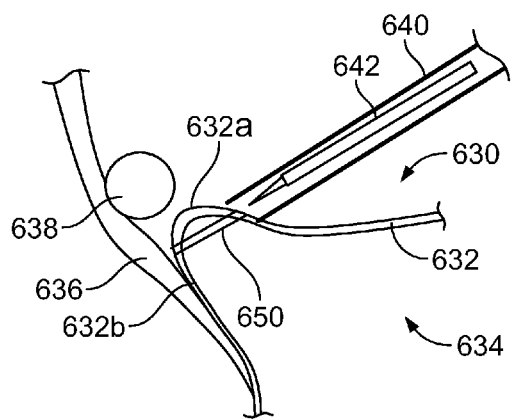
FIGS. 6a-6g are schematics showing a bi-cortical method of using a suture-based knotless repair system.
Figures 6B, 6C:
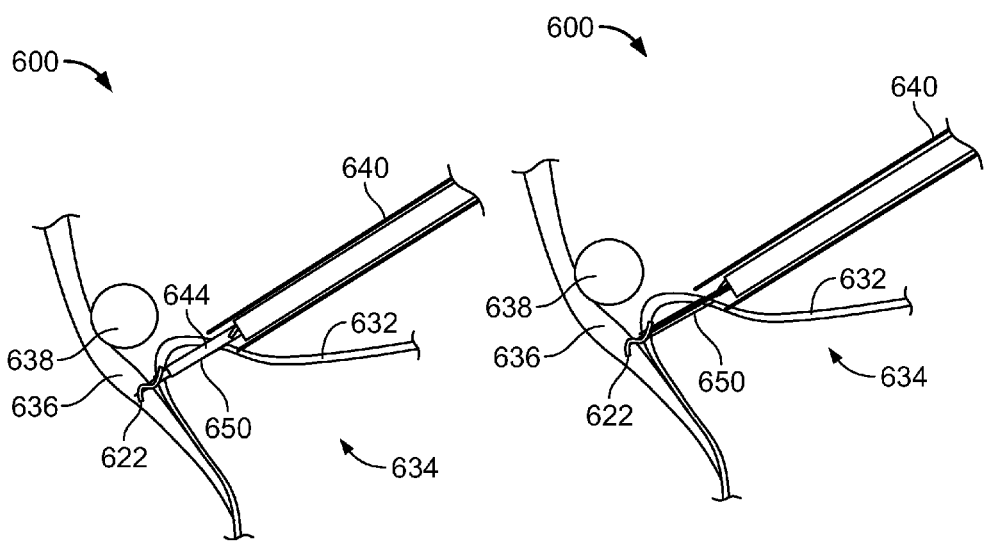

Referring to FIGS. 6a-6g, a method for using a suture-based knotless repair system 600 to make a bi-cortical labral repair, for example, in the shoulder area 630, is shown. The repair system 600 includes a suture 610 and at least two anchors 622, 624 coupled to the suture 610, and in particular, to a single loop 615 (FIG. 6f) formed by the suture 610. The suture 610 has a fixed terminal end 616 and a sliding terminal end 618 as described above (FIG. 6f). In use, preferably under arthroscopic guidance, a user inserts a drill 642 (FIG. 6a) through a guide 640 to drill a hole 650 through glenoid cortex bone 632 from a first side 632a completely through the cancellous bone tissue 634 and through the other side of the cortex bone 632b. The user can then use a first inserter needle 644 to pass the anchor 622 through the first side of the glenoid cortex bone 632a, into the cancellous bone tissue 634, and through the second side of the glenoid cortex bone 632b (FIG. 6b). When the first inserter needle 644 is removed from the tissue 632, 634 (FIG. 6c), the anchor 622 is left behind. The guide 640 is then moved and the drill can again be used (not shown) to drill a hole 652 in the labrum 638 and the capsule 636.

Figure 6D:
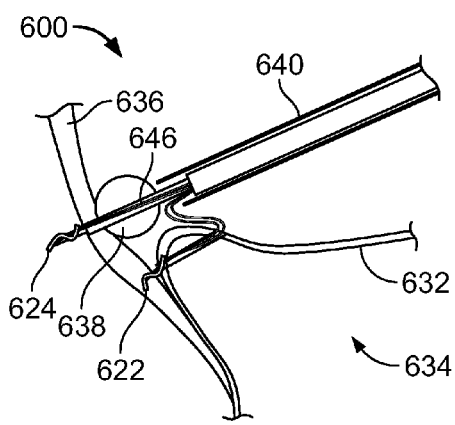
Figure 6E:
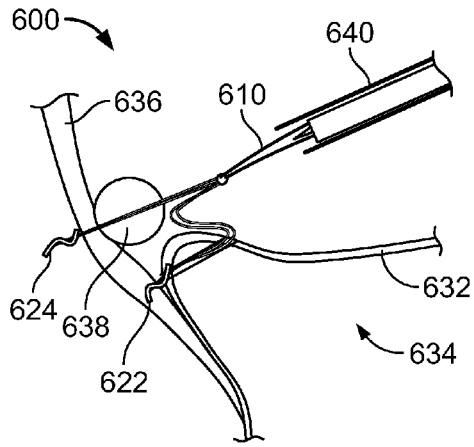
Figure 6F:
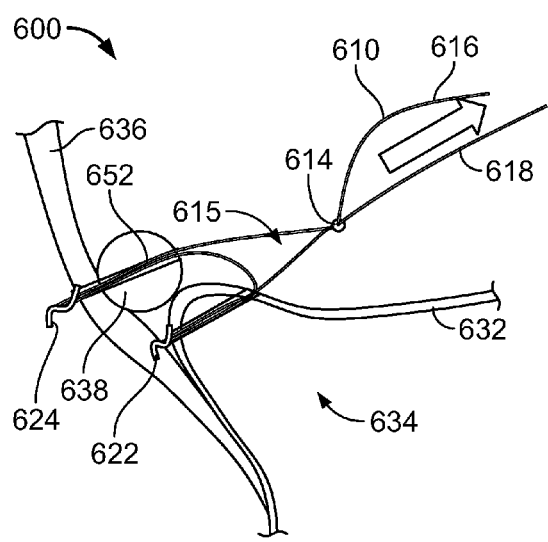
Figure 6G:
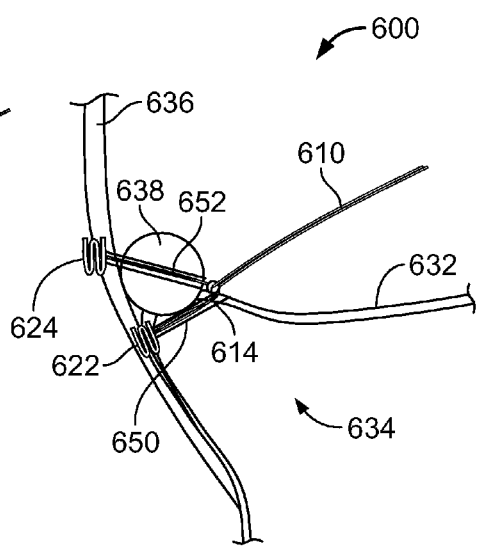

A second inserter needle 646 can be used to pass a second anchor 624 through the labrum 638 and capsule 636 (FIG. 6d). When the second inserter needle 646 is removed, the second anchor 624 is left behind (FIG. 6e). Once each of the anchors 622 and 624 have been deployed into the tissue, the user may pull the sliding terminal end 618 of the suture 610 to shorten the length of the loop 615 thus bringing the anchors 622 and 624 closer together. If flexible anchors, such as the suture anchors 622, 624, are used, the anchors will tend to bunch up as seen in FIG. 6g when force is applied to the anchors 622 and 624 from the loop 615 being pulled closed. The bunching up of the anchors 622, 624 assists in preventing pull-out of the anchors 622, 624 when the sliding terminal end 618 of the suture 610 is pulled, and provides for a more secure repair construct. A knot pusher (not shown) may also be used in conjunction with pulling on the sliding end 618 of the suture 610 to aid in closing the loop 615.

The present methods provide labral repair with linear motions: drilling, trans-cortical anchor insertion, trans-labral/capsular anchor insertion, and pulling suture(s). The methods assist in eliminating complex and time-consuming suture passing or knot tying processes, thereby reducing surgery time. These methods also allow for anterior and/or posterior approaches for accessing the tissue repair site.

Figure 7A:
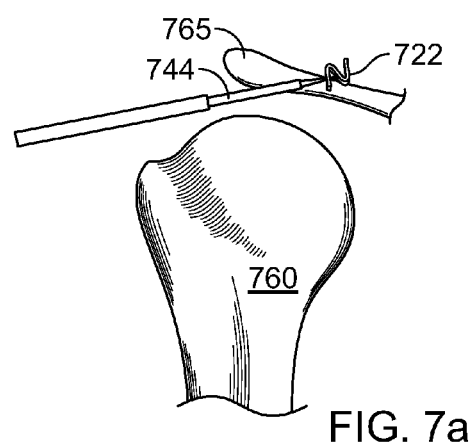
FIGS. 7a-7f are schematics showing a method of using a suture-based knotless repair system with multiple anchors.
Figure 7B:
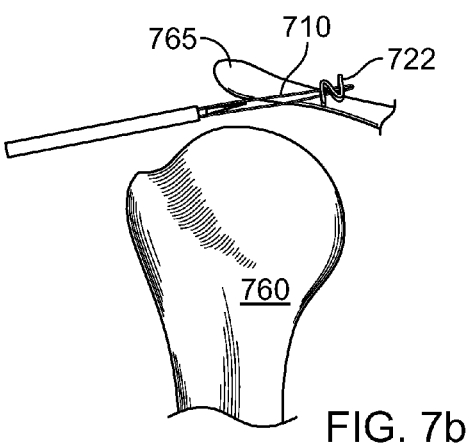
Figure 7C:
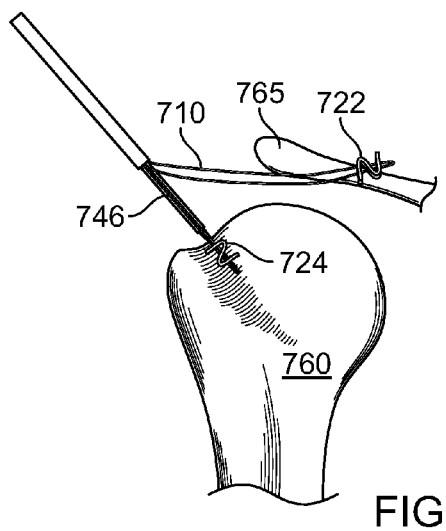
Figure 7D:
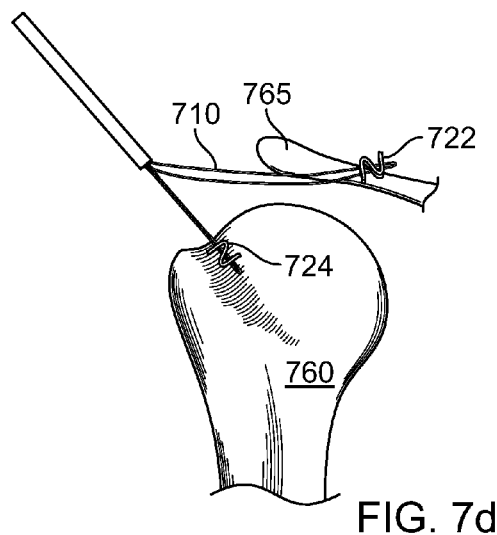
Figure 7E:
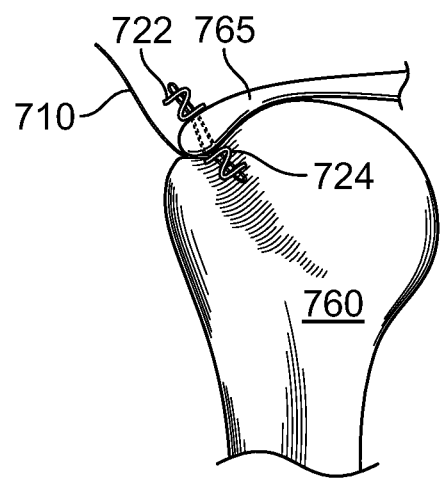
Figure 7F:
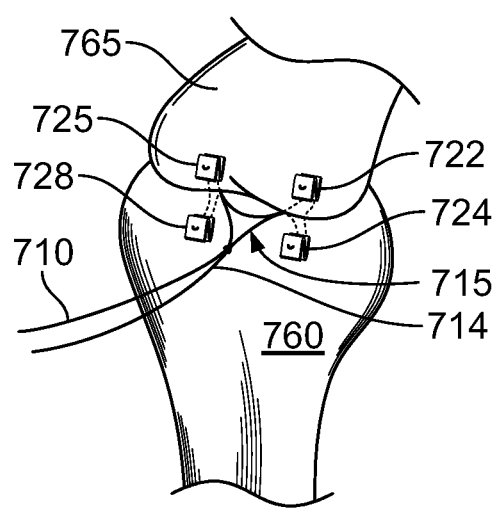
Figure 9G:
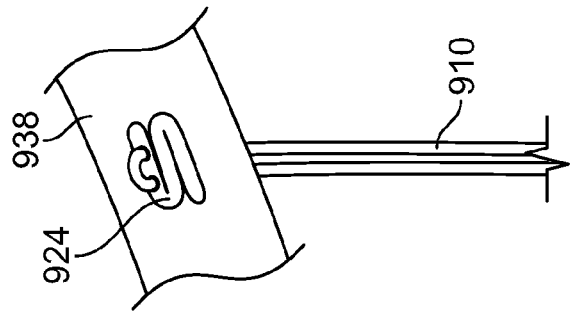

FIGS. 7a-7f show a suture-based knotless repair system having four anchors in use. The method is similar to the method shown in FIGS. 5a-5g for a system with two anchors. First, a user uses a first inserter needle 744 to pass an anchor 722 through a supraspinatus tendon 765 (FIG. 7a). When the first inserter needle 744 is removed (FIG. 7b) by, for example, sliding a slider on a delivery handle as described above, the anchor 722 is left behind in the tissue. The anchor 722 is attached to a suture 710. A second inserter needle 746 is then used to pass a second anchor 724 into the humeral head 760. When the second inserter needle 746 is removed (FIG. 9d), the second anchor 724 is left in the humeral head 760. This process is repeated with the third 725 and fourth 728 anchors. Once all of the anchors 722, 724, 725, and 728 have been deployed into the respective target tissue, one or more ends 716, 718 (FIG. 7f) of the suture 710 can be pulled in order to tighten the loop 715 in the suture 710 and bring the anchors 722, 724, 725, and 728 closer together. If flexible anchors, such as those shown, are used, the anchors will bunch up as seen in FIGS. 7e and 7f when force is applied to the anchors 722, 724, 725, and 728 from the loop 715 being pulled closed. A knot pusher (not shown) may be used to aid in closing the loop 715.

Figure 8:
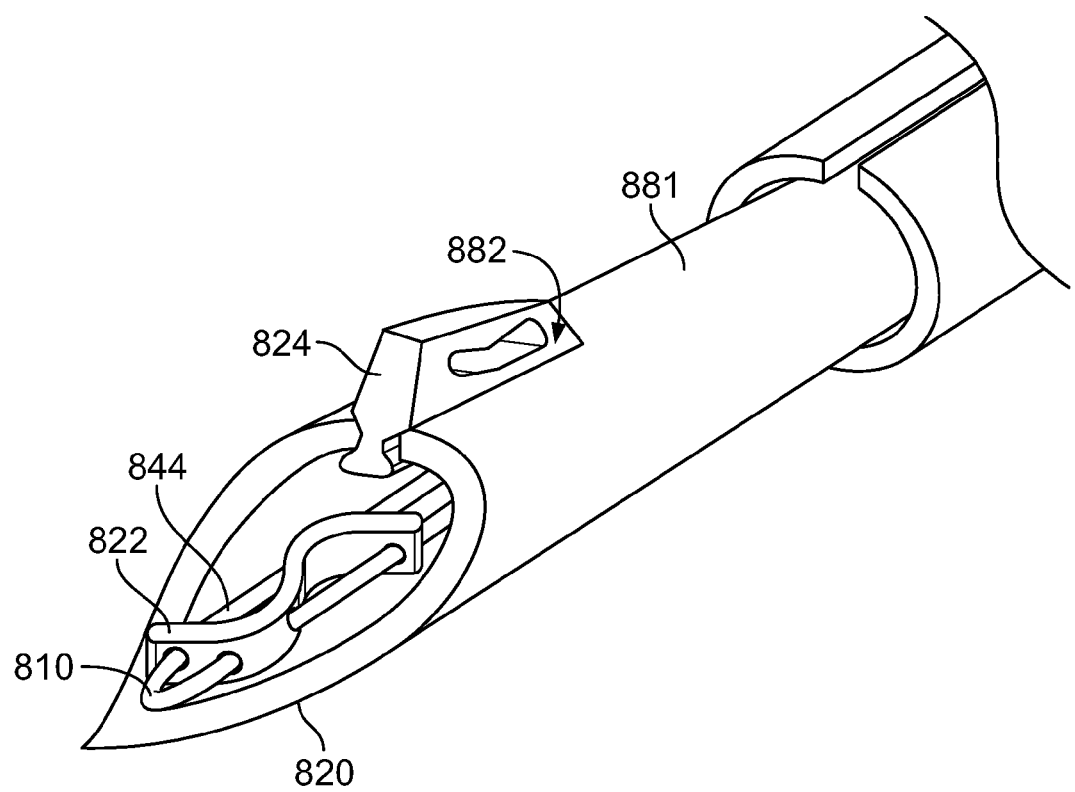
FIG. 8 is a perspective end view of another implementation of a suture-based knotless repair system.

FIG. 8 illustrates another possible implementation of the outer tube and inserter needle construction. In this implementation, the outer tube 881 has a trocar tip 820 and a slot 882 formed at a distal end of the trocar tip 820. An anchor or fixation member 824 is placed within the outer tube 881 and a portion of the anchor 824 protrudes through the slot 882 and above the outer surface of the outer tube 881. The outer tube 881 also houses at least one inserter needle 844. A second anchor 822 is loaded onto the inserter needle 844 as described above. Both anchors 822 and 824 can be connected on a single loop of a suture 810 as described above. In use, the outer tube 881 may be inserted through a tissue and then removed;

leaving behind the anchor 824 that at least partially protrudes through the slot 882 past the outer surface of the cannula 881. The anchor(s) 822 secured to inserter needle(s) can be placed as described previously with regard to FIGS. 5*a*-5*g* and 7*a*-7*f*.

In the implementation of FIG. 8, the first anchor 824 is a rigid anchor, such as one or more of the rigid anchors described in U.S. Pat. No. 7,651,509, and the second anchor 822 is a flexible anchor. Any combination of rigid and flexible anchors may be used with the suture-based knotless repair system of the present disclosure. Rigid anchors may be made of plastics including PEEK, metals including Titanium, osteo-conductive, and/or bio-absorbable materials. In addition, different shapes of anchors are contemplated such as polygonal, circular (oval), cylindrical, conical, umbrella-shaped, M-shaped, S-shaped, and/or rectangular (square) anchors. Soft or flexible anchors may include sutures or other flexible bio-compatible materials.

FIGS. 9*a*-9*c* show another implementation of an outer tube 940 and an anchor 922 used in the suture-based knotless repair system of the present disclosure. A pusher 944 is disposed within the outer tube 940. The pusher 944 may be an inserter needle such as those shown in FIGS. 3*c*-3*d*, or other suitable device to pass an anchor through the tube 940. The outer tube 940, which can have a sharpened, angled distal tip 940*a*, is inserted into and through a labrum tissue 938. The pusher 944 can then be used to pass a flexible anchor 922 through the tube 940 and labrum 938. The outer tube 940 and pusher 944 can then be removed from the labrum 938, leaving behind the anchor 922, which is connected to a suture 910. The flexible anchor 922 is in the form of an umbrella, which can collapse as it passes through the outer tube 940 and through the labrum tissue 938. Once the anchor 922 is passed into and through the labrum tissue 938, the anchor 922 can then expand (FIG. 9*c*), which prevents it from pulling back through the labrum 938 when tension is applied to the suture 910.

Figure 9F:
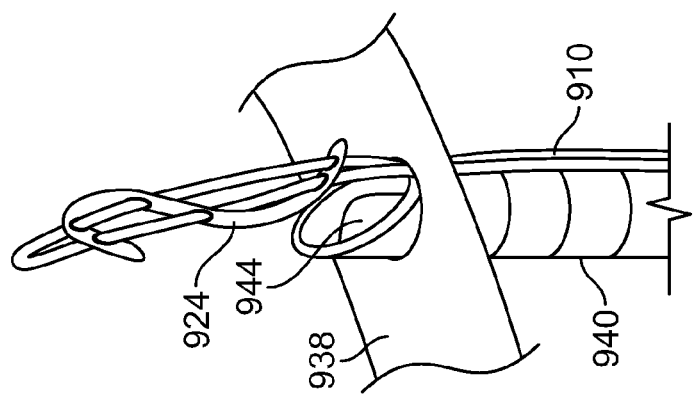
Figure 9E:
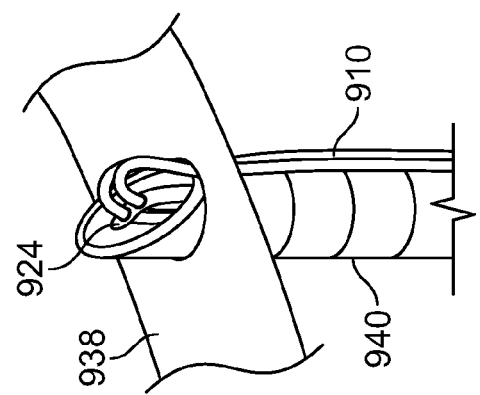
Figure 9D:
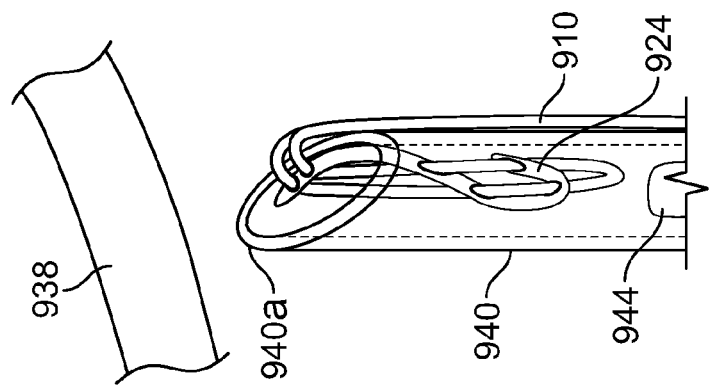

FIGS. 9*d*-9*g* show another implementation of an outer tube 940 and an anchor 924 used in the suture-based knotless repair system of the present disclosure. The anchor 924 attached on the suture 910 is installed from the proximal or distal end of the outer tube 940. The outer tube 940, which can have a sharpened, angled distal tip 940*a*, is inserted into and through a labrum tissue 938. A pusher 944 can then be used to pass the anchor 924 through the tube 940 and labrum 938 (FIG. 9*f*). The outer tube 940 and pusher 944 can then be removed from the labrum 938, leaving behind the anchor 924, which is connected to a suture 910. Once the anchor 924 is passed into and through the labrum tissue 938, the anchor 924 can then be deployed (FIG. 9*g*), which prevents it from pulling back through the labrum 938 when tension is applied to the suture 910.

Figure 10A:
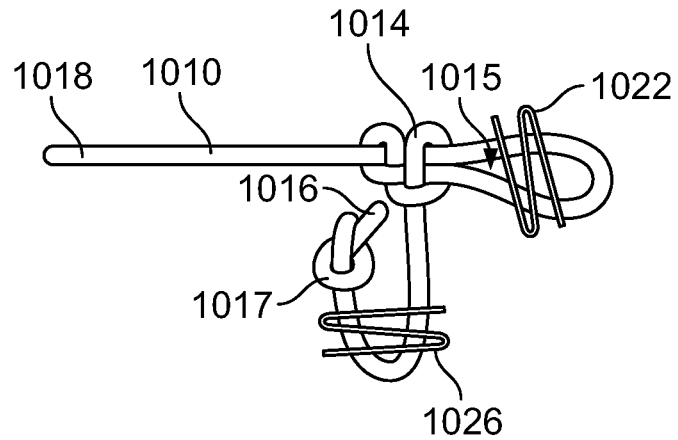
FIG. 10a is a schematic of a suture-based knotless repair system with an anchor on a terminal end of the suture and an anchor on a single closable loop.
Figure 10B:
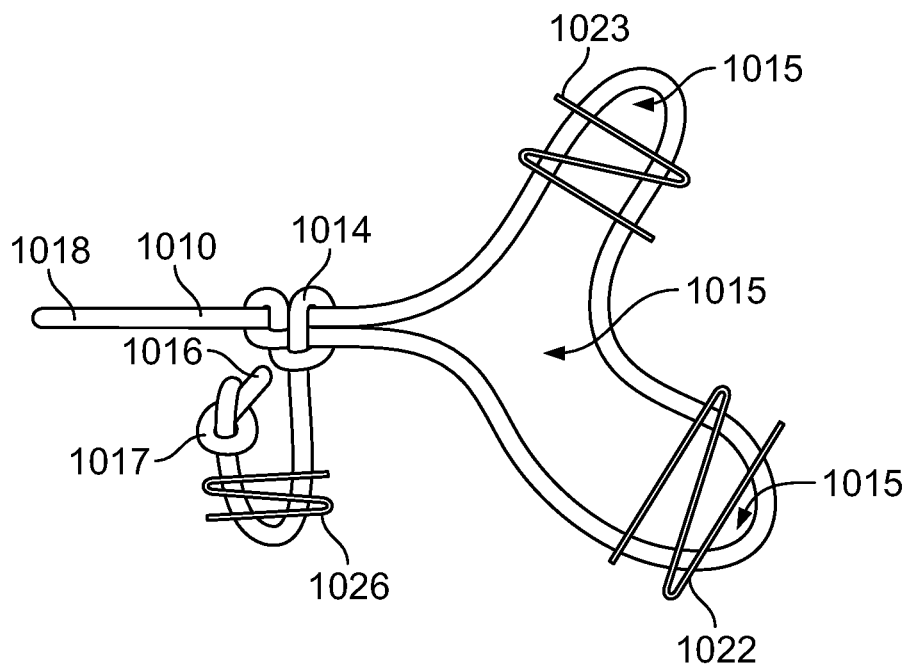
FIG. 10b is a schematic of a suture-based knotless repair system with an anchor on a terminal end of the suture and multiple anchors on a single closable loop.

While only certain implementations have been set forth, alternatives and modifications will be apparent from the above description to those skilled in the art. For example, as shown in FIG. 10*a*, instead of placing two anchors on a closed loop 1015 of the suture 1010, one anchor 1026 may be provided on the fixed terminal end 1016 of the suture 1010. This anchor 1026 is secured with, for example, a square knot 1017. The anchor 1026 can remain at a fixed distance from the slipknot 1014 or a distance from anchor 1022 while anchor 1022 on the closable loop 1015 is brought closer to the slipknot 1014 when the sliding terminal end 1018 of the suture 1010 is pulled. This may be used in surgical procedures, for example, when the known distance between the slipknot 1014 and the square knot 1017 is acceptable for tissue repair. As shown in FIG. 10*b*, in addition to having two anchors 1022, 1023 on the closed loop 1015 of the suture 1010, a third anchor 1026 may be provided on the fixed terminal end 1016 of the suture 1010. Again, the anchor 1026 can remain at a fixed distance from the slipknot 1014 or a distance from anchors 1022, 1023 while anchors 1022, 1023 on the closable loop 1015 are brought closer to the slipknot 1014.

Figure 11:
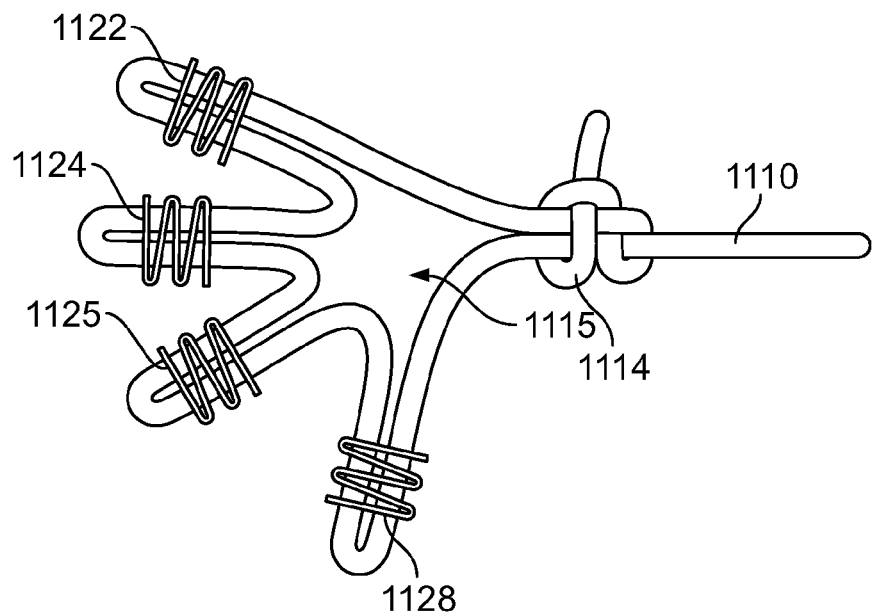
FIG. 11 is a schematic of a suture-based knotless repair system with four anchors on a single closable loop.

The present implementations also are not limited to only two anchors attached to a closable loop of the suture. For example, referring to FIG. 11, more than two anchors may be incorporated onto the closable loop 1115 as needed for a particular repair or as desired by a surgeon. FIG. 11 shows a suture-based knotless repair system having four suture anchors 1122, 1124, 1125, and 1128 attached to the closable loop 1115.

Figure 12:
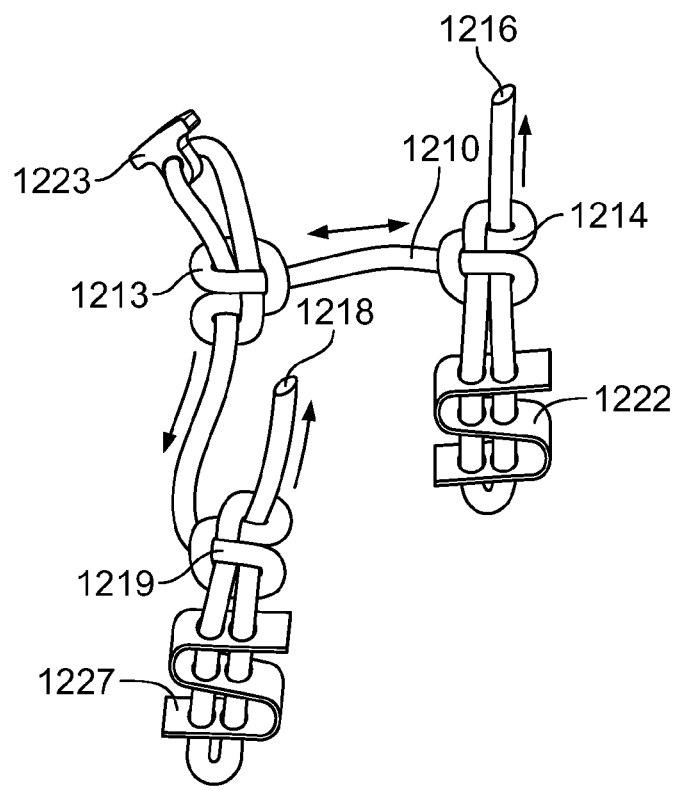
FIG. 12 is a schematic of a suture based knotless repair system with multiple loops and anchors.

In addition, the use of fixed anchors and sliding anchors can be combined to create any configuration desired such as that shown in FIG. 12. The connecting suture 1210 forms three different sliding knots 1213, 1214, and 1219. The distance between the sliding knots 1213 and 1214 is fixed, while the distance between sliding knots 1213 and 1219 can be changed. The current configuration shown in FIG. 12 shows one anchor 1222, 1223, and 1227 on each loop; however, any number of anchors may be used on any one of the loops. In this configuration, both terminal ends 1216 and 1218 of the suture 1210 are sliding terminal ends, however, one of the terminal ends could also be fixed.

Moreover, the anchors and connecting sutures can be regular bio-compatible and/or angiogenic. The inserter needles can be spring-loaded or simple sliders. A lever mechanism or a screw mechanism can be used to advance inserter needles. Additionally, the needles can be advanced manually by hand. When loading multiple anchors, the anchors can be loaded in serial or in parallel. There can be one or more connecting sutures that pass through the anchors. There can also be one or more holes on the anchors to pass the connecting suture.

These and other alternatives are considered equivalents and within the spirit and scope of this disclosure and the appended claims.

The invention claimed is:

1. An apparatus, comprising:
    a flexible member with two terminal ends, the flexible member forming a single closeable loop, the closeable loop including:
        first and second loop portions extending from opposing ends of a first bend within the closeable loop; and
        third and fourth loop portions extending from opposing ends of a second bend within the closeable loop;
    a first fixation member having two free terminal ends alternatingly extending between the first and second loop portions; and
    a second fixation member having two free terminal ends alternatingly extending between the third and fourth loop portions;
    wherein the first fixation member and the second fixation member are slidably received on the single closeable loop formed by the flexible member, such that the two free terminal ends of the first fixation member and the two free terminal ends of the second fixation member are slidable relative to the flexible member.

2. The apparatus of claim 1 wherein a length of the single closeable loop is shortened when tension is applied to one of the terminal ends of the flexible member.

3. The apparatus of claim 1 wherein the flexible member comprises a suture.

4. The apparatus of claim 1 wherein the first fixation member and the second fixation member are flexible.

5. The apparatus of claim 4 wherein the first fixation member and the second fixation member are sutures.

6. The apparatus of claim 1 wherein the first fixation member and the second fixation member are rigid.

7. The apparatus of claim 1 wherein the first fixation member is flexible and the second fixation member is rigid.

8. The apparatus of claim 1 wherein a third fixation member is coupled to one terminal end of the flexible member.

9. The apparatus of claim 1, wherein the first fixation member extends between the first and second loop portions in a zig-zag pattern and wherein the second fixation member extends between the third and fourth loop portions in a zig-zag pattern.

10. A surgical assembly comprising:
a delivery device comprising
a handle;
an outer tube, the outer tube coupled to the handle and extending from the handle; and
a first insertion needle at least partially slidably disposed within the outer tube;
a second insertion needle at least partially slidably disposed within the outer tube; and
a surgical device comprising
a flexible member with two terminal ends, forming a single closeable loop, the closeable loop including:
first and second loop portions extending from opposing ends of a first bend within the closeable loop; and
third and fourth loop portions extending from opposing ends of a second bend within the closeable loop;
a first fixation member having two free terminal ends alternatingly extending between the first and second loop portions; and
a second fixation member having two free terminal ends alternatingly extending between the third and fourth loop portions;
wherein the first fixation member and the second fixation member are slidably received on the single closeable loop formed by the flexible member such that pulling on a terminal end of the flexible member shortens a length of the flexible member between the first fixation member and second fixation members and such that the two free terminal ends of the first fixation member and the two free terminal ends of the second fixation member are slidable relative to the flexible member; and
wherein the first fixation member is releasably secured to the first insertion needle and the second fixation member is releasably secured to the second insertion needle.

11. The surgical assembly of claim 10 wherein the first fixation member and the second fixation member are flexible fixation members.

12. The surgical assembly of claim 11 wherein the first fixation member and the second fixation member are sutures.

13. The surgical assembly of claim 10
wherein the first insertion needle defines a notch configured to receive the first fixation member and the second insertion needle defines a notch configured to receive the second fixation member; and
wherein the first fixation member is releasably secured to the first insertion needle by inserting a portion of the first fixation member into the notch defined by the first insertion needle and the second fixation member is releasably secured to the second insertion needle by inserting a portion of the second fixation member into the notch defined by the second insertion needle.

14. The surgical assembly of claim 10, further comprising a first switch slidably positioned within the handle and coupled to the first insertion needle; and
a second switch slidably positioned within the handle and coupled to the second insertion needle.

15. A surgical assembly comprising:
a delivery device comprising
a handle;
a tubular needle, the tubular needle extending from the handle and defining:
a longitudinal channel; and
a trocar tip; and
a pusher disposed at least partially within the tubular needle; and
a surgical device comprising
a flexible member with two terminal ends, the flexible member forming a single closeable loop, the closeable loop including:
first and second loop portions extending from opposing ends of a first bend within the closeable loop; and
third and fourth loop portions extending from opposing ends of a second bend within the closeable loop;
a first fixation member having two free terminal ends alternatingly extending between the first and second loop portions; and
a second fixation member having two free terminal ends alternatingly extending between the third and fourth loop portions;
wherein the first fixation member and the second fixation member are slidably received on the single closeable loop such that pulling on a terminal end of the flexible member shortens a length of the flexible member between the first fixation member and the second fixation member, and such that the two free terminal ends of the first fixation member and the two free terminal ends of the second fixation member are slidable relative to the flexible member wherein the first fixation member is secured to the pusher; and
wherein the second fixation member protrudes through an outer surface of the tubular needle, and the flexible member passes through the longitudinal channel.

16. The surgical assembly of claim 15 wherein the pusher defines a notch configured to receive the first fixation member and wherein the first fixation member is secured to the pusher by inserting a portion of the first fixation member into the notch defined by the pusher.

17. The surgical assembly of claim 15, further comprising a switch slidably positioned within the handle.

18. The surgical assembly of claim 17 wherein the switch is coupled to a proximal end of the pusher.

19. The surgical assembly of claim 15 wherein the first fixation member is a flexible fixation member and the second fixation member is a rigid fixation member.

20. The surgical assembly of claim 15 wherein the first fixation member is a suture.

21. The surgical assembly of claim 15 wherein the pusher is an inserter needle.

22. The surgical assembly of claim 15, wherein the tubular needle further comprises a slot formed at a distal end of the trocar tip, wherein the second fixation member protrudes through the slot.

* * * * *